United States Patent
Naya

(10) Patent No.: US 7,224,451 B2
(45) Date of Patent: May 29, 2007

(54) RAMAN SPECTROSCOPY METHOD, RAMAN SPECTROSCOPY SYSTEM AND RAMAN SPECTROSCOPY DEVICE

(75) Inventor: Masayuki Naya, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 203 days.

(21) Appl. No.: 11/029,016

(22) Filed: Jan. 5, 2005

(65) Prior Publication Data

US 2006/0001872 A1 Jan. 5, 2006

(30) Foreign Application Priority Data

Jan. 7, 2004 (JP) .............................. 2004-001553

(51) Int. Cl.
*G01J 3/44* (2006.01)
*G01N 21/65* (2006.01)

(52) U.S. Cl. ..................................... 356/301
(58) Field of Classification Search ................. 356/301
See application file for complete search history.

(56) References Cited

FOREIGN PATENT DOCUMENTS

| JP | 2003-268592 A | 9/2003 |
|---|---|---|
| JP | 2004-232027 A | 8/2004 |
| WO | WO 01/06257 A1 | 1/2001 |

OTHER PUBLICATIONS

Brolo et al., Nanohole-Enhanced Raman Scattering, NANO Letters, vol. 4, No. 10, 2004, Published on Web Sep. 11, 2004.*
"Brilliant Optical Properties of Nanometric Noble Metal Spheres, Rods, and Aperture Arrays", Peter C. Andersen, et al., Applied Spectroscopy, vol. 56, No. 5, pp. 124A-135A, May 2002.

Haynes C L et al: "Nanosphere lithography: synthesis and application of nanoparticles with inherently anisotropic structures and surface chemistry", Anisotropic Nanoparticles—Synthesis, Characterization and applications. Symposium (Materials Research Society Symposium Proceedings vol. 635) Mater. Res Soc Warrendale, PA, USA, 'Online! 2001, pp. C6.3. 1-6, XP002324693.
Mulvaney S P et al: "Three-layer substrates for surface-enhanced Raman scattering: preparation and preliminary evaluation" Journal of Raman Spectroscopy Wiley UK 'Online!, vol. 34, No. 2, 2003, pp. 163-171, XP002324694.

* cited by examiner

*Primary Examiner*—F. L. Evans
(74) *Attorney, Agent, or Firm*—Sughrue Mion, PLLC

(57) ABSTRACT

In a Raman spectroscopy, the surface of metal film which is formed on a dielectric substrate in thickness of 50 to 200 nm and is characterized in that a plurality of fine holes satisfying the conditions defined by the following formulae are formed is caused to adsorb the material to be analyzed, light is projected onto the surface and the scattering light scattered by the surface is separated to obtain a spectrum of the scattering light, $$\lambda = a\left(\frac{\varepsilon 1 \cdot \varepsilon 2}{\varepsilon 1 + \varepsilon 2}\right)^{\frac{1}{2}}$$

$$d < \lambda$$

wherein $\lambda$ represents the wavelength of the projected light, a represents the cycle of the fine holes, d represents the diameter of the fine holes, $\varepsilon 1$ represents the dielectric constant of the metal film and $\varepsilon 2$ represents the dielectric constant of the medium around the surface of the metal film.

4 Claims, 1 Drawing Sheet

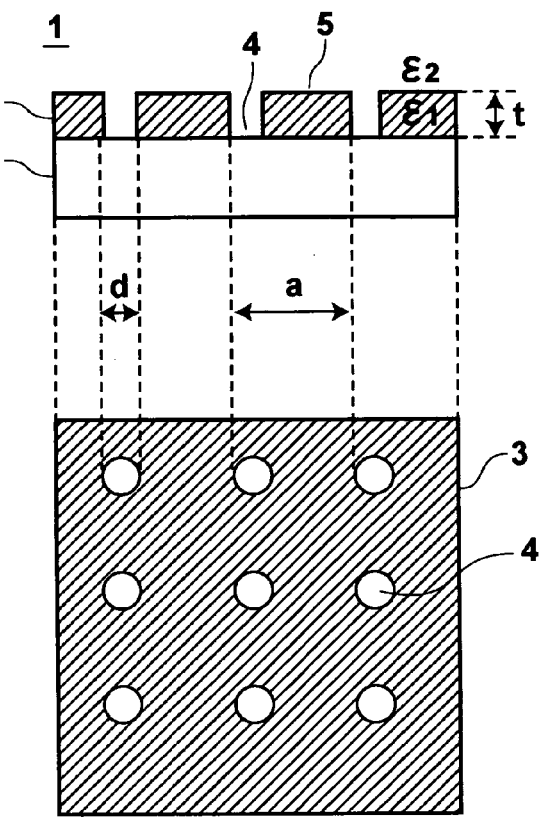
FIG.1A
FIG.1B
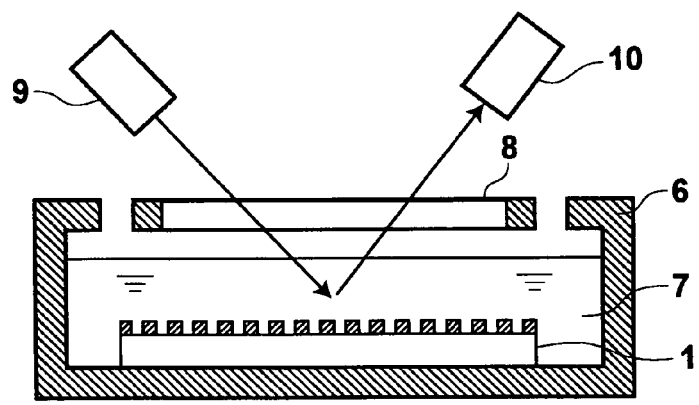
FIG.2
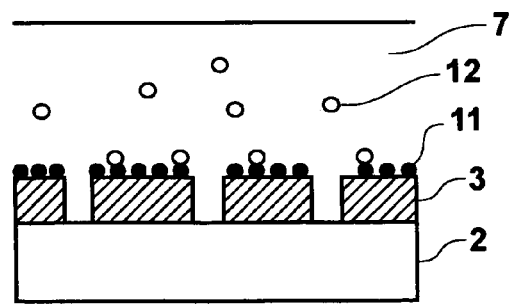
FIG.3

RAMAN SPECTROSCOPY METHOD, RAMAN SPECTROSCOPY SYSTEM AND RAMAN SPECTROSCOPY DEVICE

BACKGROUND OF THE INVENTION

1. Field of the Invention

This invention relates to a Raman spectroscopy method, a Raman spectroscopy system and a Raman spectroscopy device and more particularly to a Raman spectroscopy device for increasing Raman scattering.

2. Description of the Related Art

The Raman spectroscopy method is a method where a spectrum (Raman spectrum) is obtained by separating scattering light obtained by projecting light of a single wavelength onto a material and light (Raman scattering light) having a wavelength different from that of the projected light is detected. Since being very weak, the Raman scattering light is generally difficult to detect. However, it has been reported that the intensity of the Raman scattering light is increased to $10^4$ to $10^6$ when light is projected onto the material adsorbed on the surface of metal. Especially it has been known that when metal particles in the order of nanometers are distributed on the surface on which the material is adsorbed, the Raman scattering light is greatly increased. See, for instance, "Brilliant Optical Properties of Nanometric Noble Metal Spheres, Rods, and Aperture Arrays", Peter C. Andersen and Kathy L. Rowlen, Applied Spectroscopy, Volume 56, Number 5, 2002. The increase of the Raman scattering light is said to be due to local plasmon resonance. That is, it is said that strong electric fields are generated around metal particles when the free electrons in the metal particles vibrate resonating with an electric field of light, and the Raman scattering light is increased under the influence of the electric fields.

SUMMARY OF THE INVENTION

The object of the present invention is to propose a structure of the metal surface which can increase the Raman scattering light more effectively than the structure where metal particles are distributed, and more facilitate detection of the Raman scattering light.

In the Raman spectroscopy, a spectrum is obtained by separating scattering light obtained by projecting light of a predetermined wavelength onto a material and light having a wavelength different from that of the projected light is detected. In accordance with this invention, the Raman spectroscopy is carried out with the material to be analyzed being adsorbed on the surface of a device having the following structure.

The Raman spectroscopy device of the present invention comprises a dielectric substrate and metal film formed on the substrate in thickness of 50 to 200 nm and is characterized in that a plurality of fine holes satisfying the conditions defined by the following formulae (1) and (2) are formed in the metal film.

$$\lambda = a\left(\frac{\varepsilon 1 \cdot \varepsilon 2}{\varepsilon 1 + \varepsilon 2}\right)^{\frac{1}{2}} \quad (1)$$

$$d < \lambda \quad (2)$$

In the above formulae, $\lambda$ represents the wavelength of the projected light, $a$ represents the cycle of the fine holes, and $d$ represents the diameter of the fine holes. The cycle of the fine holes is expressed in terms of distances between adjacent fine holes (e.g., a distance between the center of a given fine hole and the center of an adjacent fine hole. Further, $\varepsilon 1$ represents the dielectric constant of the metal film and $\varepsilon 2$ represents the dielectric constant of the medium around the surface of the metal film. For instance, when the device is in air, the medium around the surface of the metal film is the air and when the device is in a solution, then the medium around the surface of the metal film is the solution.

The above formulae (1) and (2) represent conditions under which the light is confined in the device. The free electrons in the metal film vibrate resonating with an electric field of the light and generate an electric field around the metal film. When the light is confined in the device, the light is best used and the electric field generated around the metal film is maximized. The Raman scattering light is increased under the influence of the electric field around the metal film as described above. Accordingly, by the use of the light confining effect, the Raman scattering light can be more increased.

In accordance with the method of the present invention, the Raman spectroscopy is carried out on the basis of the above principle. That is, the method of the present invention comprises the steps of causing the surface of metal film which is formed on a dielectric substrate in thickness of 50 to 200 nm and is characterized in that a plurality of fine holes satisfying the conditions defined by the above formulae (1) and (2) are formed to adsorb the material to be analyzed, projecting light onto the surface and separating the scattering light scattered by the surface to obtain a spectrum of the scattering light. In order to project light of a wavelength $\lambda$ onto the surface on which the material-to-be-analyzed is adsorbed, it is preferred that light of a single wavelength of $\lambda$ be projected onto the surface but light whose central wavelength $\lambda 0$ is in the range represented by the following formula may be projected.

$$\lambda 0 = a\left(\frac{\varepsilon 1 \cdot \varepsilon 2}{\varepsilon 1 + \varepsilon 2}\right)^{\frac{1}{2}} \pm 20 \text{ nm} \quad (3)$$

The system of the present invention is a Raman spectroscopy system in which a spectrum is obtained by separating scattering light obtained by projecting light of a wavelength of $\lambda$ onto a material and light having a wavelength different from $\lambda$ is detected, and comprises a Raman spectroscopy device provide with a dielectric substrate and metal film formed on the substrate in thickness of 50 to 200 nm and provided with a plurality of fine holes satisfying the conditions defined by the above formulae (1) and (2), a light projecting means which projects light onto the surface of the Raman spectroscopy device in which the fine holes are formed and a spectral means which separates the light projected by the light projecting means and scattered by the surface to obtain a spectrum of the scattering light.

In the Raman spectroscopy device, almost all the projected light is used to strengthen the intensity of the electric fields around the device since the device is of a structure in which the light is confined in the device. That is, the intensity of the electric fields around the device is strengthened by the best use of energy of the projected light, and the Raman scattering light can be effectively increased by the electric fields.

In the Raman spectroscopy method and the Raman spectroscopy system of the present invention, since a Raman spectroscopy is carried out by the use of such a Raman spectroscopy device, the Raman scattering light can be accurately detected.

BRIEF DESCRIPTION OF THE DRAWINGS

FIG. 1A is a cross-sectional view of a Raman spectroscopy device in accordance-with an embodiment of the present invention, FIG. 1B is a plan view of a Raman spectroscopy device in accordance with the embodiment of the present invention, FIG. 2 is a view for illustrating a Raman spectroscopy method and a Raman spectroscopy system in accordance with an embodiment of the present invention, and FIG. 3 is a view for illustrating a Raman spectroscopy method in accordance with another embodiment of the present invention.

DESCRIPTION OF THE PREFERRED EMBODIMENTS

A Raman spectroscopy device 1 in accordance with an embodiment of the present invention comprises a dielectric base plate 2 and metal film 3 formed on the base plate 2 as shown in FIG. 1A. It is preferred that the metal film 3 is of a noble metal such as gold (Au), silver (Ag), copper (Cu), nickel (Ni), cobalt (Co) or the like. The thickness t of the metal film 3 is about 50 to 200 nm and a plurality of fine holes 4 formed in the surface of the metal film 3 at predetermined intervals as shown in FIG. 1B. Each of the fine holes 4 extends through the metal film 3 to expose the dielectric base plate 2 as shown in FIG. 1A.

It has been reported by T. W. Ebbesen and et. al. that the device 1 of this structure exhibits an abnormal light transmission when light of a wavelength longer than the diameter of the fine holes 4 is projected onto the surface. (Nature 391, 667, 1998) Further, this phenomenon is considered to be due to the surface plasmon since this phenomenon is not caused when the metal film is too thick or the film on the surface of the device is of material other than metal.

Theses inventors have conceived from the report that when the diameter d of the fine holes 4 is made smaller than the wavelength of the projected light to increase the light transmissivity, the amount of light which is confined in the metal film to contribute to generation of the surface plasmon resonance is increased to generate a strong electric field on the surface of the device and the Raman scattering light can be greatly amplified by the use of the electric field.

The light transmissivity is maximized when the relation between the cycle a of the fine holes 4 and the wavelength $\lambda$ satisfies the following formula wherein $\epsilon 1$ represents the dielectric constant of the metal film 3 and $\epsilon 2$ represents the dielectric constant of the medium 5 around the surface of the metal film 3.

$$\lambda = a\left(\frac{\varepsilon 1 \cdot \varepsilon 2}{\varepsilon 1 + \varepsilon 2}\right)^{\frac{1}{2}}$$

Accordingly, by selecting a device provided with fine holes having an optimal diameter and formed at an optimal cycle according to the wavelength $\lambda$ of the light to be projected, a great Raman increasing effect can be obtained and the Raman scattering light can be accurately detected.

The device 1 can be produced by forming a metal film 3 on a dielectric base plate 2 by deposition or sputtering and subsequently forming fine holes 4 in the metal film 3 by fine processing technology such as exposure to electron radiations, proximity field lithography or nano-imprinting.

A Raman spectroscopy system employing the device 1 shown in FIGS. 1A and 1B and a method employing the Raman spectroscopy system to carry out the Raman spectroscopy will be described, hereinbelow.

FIG. 2 shows a Raman spectroscopy system in accordance with an embodiment of the present invention. As shown in FIG. 2, the system comprises a container 6 with a transparent window 8, a device 1 fixed to the bottom of the container 6, a laser 9 which projects a laser beam toward the device 1 in the container 6, and a spectral photodetector 10 which separates the scattering light scattered by the surface of the device 1 to obtain a spectrum of the scattering light. The laser 9 is adjusted in advance so that the central wavelength of the laser beam is in the range defined by the following formula.

$$\lambda 0 = a\left(\frac{\varepsilon 1 \cdot \varepsilon 2}{\varepsilon 1 + \varepsilon 2}\right)^{\frac{1}{2}} \pm 20 \text{ nm}$$

The device 1 is positioned so that the metal film 3 provided with the fine holes 4 is directed upward. When carrying out the spectroscopy, sample solution 7 to be analyzed is filled in the container 6 so that the material-to-be-analyzed contained in the sample solution 7 is adsorbed on the surface of the device 1.

When a laser beam is projected onto the device 1 through the transparent window 8 from the laser 9, the laser beam is scattered by the surface of the device 1 and the scattering light is detected by the spectral photodetector 10. The spectral photodetector 10 separates the detected scattering light and generates a Raman spectrum. The generated Raman spectrum is output to a display or a printer (not shown).

A material which is bonded with a specific material may be fixed to the metal film 3 of the device 1. For example, when antibody 11 is fixed to the surface of the metal film 3 as shown in FIG. 3, the spectrum obtained by separation of the scattering light greatly changes if antigen 12 is brought into contact with the surface due to chemical bond of the antibody 11 and the antigen 12. When the Raman scattering light is increased by the device 1, the spectrum greatly changes, whereby the identification and/or the analysis of the molecular mechanism of the antigen can be accurately effected.

As can be understood from the description above, when the Raman spectroscopy is carried out by the Raman spectroscopy system employing the device 1, the Raman scattering light can be accurately detected since the Raman scattering light is increased, and an accurate spectrum can be obtained. Since the Raman spectroscopy has been in wide use in all the fields to identify material and/or to determine the molecular mechanism of material, the device, the Raman spectroscopy system and the Raman spectroscopy method described above are highly useful.

What is claimed is:

1. A Raman spectroscopy method in which a spectrum is obtained by separating scattering light obtained by projecting light of a wavelength of $\lambda$ onto a material and light having a wavelength different from $\lambda$ is detected, the method comprising the steps of causing the surface of metal film which is formed on a dielectric substrate in thickness of 50 to 200 nm and is characterized in that a plurality of fine holes satisfying the conditions defined by the following formulae are formed to adsorb the material to be analyzed, projecting light onto the surface and separating the scattering light scattered by the surface to obtain a spectrum of the scattering light, $$\lambda = a\left(\frac{\varepsilon 1 \cdot \varepsilon 2}{\varepsilon 1 + \varepsilon 2}\right)^{\frac{1}{2}}$$

$d<\lambda$ wherein $\lambda$ represents the wavelength of the projected light, a represents the cycle of the fine holes, d represents the diameter of the fine holes, $\epsilon 1$ represents the dielectric constant of the metal film and $\epsilon 2$ represents the dielectric constant of the medium around the surface of the metal film.

2. A Raman spectroscopy method as defined in claim 1 in which light whose central wavelength $\lambda 0$ is in the range represented by the following formula is projected, $$\lambda 0 = a\left(\frac{\varepsilon 1 \cdot \varepsilon 2}{\varepsilon 1 + \varepsilon 2}\right)^{\frac{1}{2}} \pm 20 \text{ nm.}$$

3. A Raman spectroscopy system in which a spectrum is obtained by separating scattering light obtained by projecting light of a wavelength of $\lambda$ onto a material and light having a wavelength different from $\lambda$ is detected, the system comprising a Raman spectroscopy device provided with metal film which is formed on a dielectric substrate in thickness of 50 to 200 nm and is characterized in that a plurality of fine holes satisfying the conditions defined by the following formulae are formed, a light projecting means which projects light onto the surface of the Raman spectroscopy device in which the fine holes are formed and a spectral means which separates the light projected by the light projecting means and scattered by the surface to obtain a spectrum of the scattering light, $$\lambda = a\left(\frac{\varepsilon 1 \cdot \varepsilon 2}{\varepsilon 1 + \varepsilon 2}\right)^{\frac{1}{2}}$$

$d<\lambda$ wherein $\lambda$ represents the wavelength of the projected light, a represents the cycle of the fine holes, d represents the diameter of the fine holes, $\epsilon 1$ represents the dielectric constant of the metal film and $\epsilon 2$ represents the dielectric constant of the medium around the surface of the metal film.

4. A Raman spectroscopy device for use in a Raman spectroscopy in which a spectrum is obtained by separating scattering light obtained by projecting light of a wavelength of $\lambda$ onto a material and light having a wavelength different from $\lambda$ is detected, the device comprising a dielectric substrate and metal film formed on the substrate in thickness of 50 to 200 nm and is characterized in that a plurality of fine holes satisfying the conditions defined by the following formulae are formed, $$\lambda = a\left(\frac{\varepsilon 1 \cdot \varepsilon 2}{\varepsilon 1 + \varepsilon 2}\right)^{\frac{1}{2}}$$

$d<\lambda$ wherein $\lambda$ represents the wavelength of the projected light, a represents the cycle of the fine holes, d represents the diameter of the fine holes, $\epsilon 1$ represents the dielectric constant of the metal film and $\epsilon 2$ represents the dielectric constant of the medium around the surface of the metal film.

* * * * *